United States Patent [19]

Miller et al.

[11] Patent Number: 4,529,500
[45] Date of Patent: Jul. 16, 1985

[54] METHOD FOR MINIMIZING FOULING OF HEAT EXCHANGER

[75] Inventors: Richard F. Miller, Humble; Michael P. Nicholson, Houston, both of Tex.

[73] Assignee: Atlantic Richfield, Los Angeles, Calif.

[21] Appl. No.: 639,892

[22] Filed: Aug. 10, 1984

[51] Int. Cl.$^3$ .............................................. C07C 7/18
[52] U.S. Cl. .................... 208/48 AA; 203/8; 203/9; 544/35; 544/37; 585/2; 585/3; 585/4; 585/5; 585/865; 585/952
[58] Field of Search .............. 544/35, 37; 208/48 AA; 585/2, 3, 4, 5, 864, 865, 866, 867, 952; 203/8, 7, 203/9

[56] References Cited

U.S. PATENT DOCUMENTS

| | | | |
|---|---|---|---|
| 3,275,531 | 9/1966 | Sennewald et al. | 203/8 |
| 3,329,582 | 1/1967 | Sennewald et al. | 203/8 |
| 3,539,515 | 11/1970 | McCabe | 252/47.5 |
| 3,689,484 | 9/1972 | Spilners | 544/35 |
| 3,794,567 | 2/1974 | Otsuki et al. | 203/8 |
| 3,969,289 | 5/1976 | McGuigan et al. | 544/37 |
| 4,021,310 | 5/1977 | Shimizu et al. | 203/8 |
| 4,061,545 | 12/1977 | Watson | 585/864 |
| 4,177,110 | 12/1979 | Watson | 585/5 |
| 4,465,881 | 8/1984 | Miller et al. | 585/2 |

Primary Examiner—D. E. Gantz
Assistant Examiner—A. Pal
Attorney, Agent, or Firm—Coleman R. Reap

[57] ABSTRACT

Hydrocarbon processing equipment is protected against fouling during the processing of hydrocarbons at elevated temperatures by adding to the equipment small amounts of the N,N'-dimer of phenothiazine or a substituted phenothiazine.

4 Claims, No Drawings

METHOD FOR MINIMIZING FOULING OF HEAT EXCHANGER

FIELD OF THE INVENTION

This invention relates to antifoulants and to a method of inhibiting fouling in petroleum or petroleum derivative processing equipment by injecting an antifoulant composition into a feed stream of the material being processed.

RELATED CASES

U.S. application Ser. No. 530,294, filed 9/8/83, relates to the use of N,N'-dimers of phenothiazine to prevent the undesired polymerization of vinyl aromatic compounds.

BACKGROUND

Fouling of heat transfer surfaces of petroleum processing equipment occurs continuously during the period when petroleum or its derivatives are being processed in the equipment. The fouling is caused by the gradual buildup of a layer of high molecular weight polymeric material resulting from the thermal degradation of certain hydrocarbon materials which are present in the petroleum. As time goes by, fouling continues with the attendant loss of heat transfer until finally the point is reached where it becomes necessary to take the equipment out of service for cleaning. Cleaning is expensive and time consuming; consequently, methods of preventing fouling, or at least significantly reducing the rate of fouling, are constantly being sought.

The most economical method of reducing the fouling rate in process heat transfer equipment is to add chemicals which inhibit fouling, called "antifoulants", to the feed stream being processed. Among the more interesting classes of chemical compounds which exhibit antifoulant activity are the phenothiazines. Their use to inhibit polymerization has been described in patents.

PRIOR ART

U.S. Pat. Nos. 4,061,545 and 4,177,110 issued to Watson, disclose the use of a combination of tertiary-butylcatechol and phenothiazine as a polymerization inhibitor system for vinyl aromatic compounds. U.S. Pat. No. 3,539,515, issued to McCabe, discloses the use of phenothiazine dehydrocondensates as antioxidants for lubricating oils. The phenothiazine dehydrocondensates are prepared by reacting phenothiazine or a substituted phenothiazine with an organic peroxide.

It has now been discovered that N'N'-dimers of phenothiazine or substituted phenothiazines provide outstanding antifoulant protection for petroleum and petroleum derivative processing equipment.

Accordingly, it is an object of the invention to present a method of enhancing the antifouling protection of petroleum processing equipment. This and other objects of the invention are set forth in the following description and examples of the invention.

SUMMARY OF THE INVENTION

The antifoulants used in the invention are the N,N'-dimers of phenothiazine or substituted phenothiazines. In a perferred embodiment of the invention the antifoulant is dissolved in an organic solvent and the resulting solution is continuously injected into a stream of petroleum at a point which is upstream from the equipment which is to be protected.

DETAILED DESCRIPTION OF THE INVENTION

The N,N'-dimers of phenothiazine or the substituted phenothiazines most useful in the invention have the structural formula

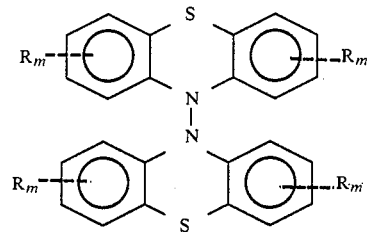

wherein m is an integer of 0 to 4, i.e. there may be from 0 to 16 R substituents on each molecule of the dimer, and some or all of the R's may be identical or all of the R's may be different. In the preferred embodiment the m's are integers having values of 0, 1 or 2. Each R may be a halogen atom or an unsubstituted or a halogen-substituted alkyl group having 1 to 20 and preferably 1 to 6 alkyl carbon atoms.

When all of the m's in the above structural formula are 0, the compound is the N,N' dimer of phenothiazine. This is the preferred embodiment of the invention since unsubstituted phenothiazine is less expensive as a starting material than the substituted phenothiazines. In alternate embodiments the m's may be integers of 1 to 4, in which case the compound is a dimer of halogen-substituted, alkyl-substituted or haloalkyl-substituted derivative of phenothiazine. Typical hydrocarbon alkyl substituents include methyl, ethyl, isopropyl, butyl, hexyl decyl, hexadecyl, etc. groups. There may be up to 4 such substituents on each benzene ring portion of the dimer. Since the dimer contains 4 benzene nuclei there may be up to 16 identical or different substituents. If all of the starting material is phenothiazine or a single derivative of phenothiazine, the dimer is composed of two identical moieties. However, if the starting material is composed of two or more different starting materials a mixture of products would result some of which could have 16 different substituents if the monomeric starting materials have all dissimilar substituents.

Typical phenothiazine dimers are 10,10'diphenothiazine; 1,1'-dimethyl-10,10'-diphenothiazine; 2,6,2',6'-tetramethyl-10,10'-diphenothiazine; 2,2'-dimethyl-8,8'-dipropyl-10,10'diphenothiazine; 3,4'-dimethyl, 1,6,7'dihexyl-10,10'diphenothiazine; 2,2'-dichloro-10,10'-diphenothiazine; 3,3',7,7'-tetrabromo-10,10'-diphenothiazine; 4,4'-bis(2-chloroethyl)-10,10'-diphenothiazine; 3,3',6,6'-tetrakis(4-flourobutyl)-10,10'-diphenothiazine; 1,1',2,2',3,3',4,4',6,6',7,7',8,8',9,9'-hexadecylmethyl-10,10'-diphenothiazine; etc. From the standpoint of preparation, cost and utility, the preferred phenothiazine dimers are phenothiazine dimer and the alkyl-substituted phenothiazine dimers having up to two substituents on each benzene nucleus, each substituent having 1 to 6 carbon atoms in each alkyl group. Examples of preferred substituted phenothiazine dimers are 1,1'-dimethyl-10,10'-diphenothiazine, 2,2'dimethyl-4,4'-diethyl-10,10'diphenothiazine; 2,2',6,6'tetramethyl-3,3'-diethyl-10,10'diphenothiazine, etc.

The term "phenothiazine component" as used herein represents phenothiazine or any of the substituted phenothiazines in the above definition.

Phenothiazine and some hydrocarbon-substituted phenothiazines are available commercially. Others may be prepared by well-known techniques, such as alkylation. The preparation of the phenothiazine component forms no part of the present invention.

The phenothiazine dimers used in the invention are prepared by heating the phenothiazine component in the presence of an organic peroxide. The optimum reaction temperature employed will vary depending upon the particular phenothiazine compound used as the starting material and the particular organic peroxide used. In general, temperatures in the range of about 25 to 300° C. are effective to produce the desired result.

Any of the common organic peroxides can be used to effect the dimerization. The peroxide chosen will depend upon the desired reaction temperature. Typical organic peroxides include benzoyl peroxide, lauroyl peroxide, di-tertiary-butyl peroxide, tertiary-butyl hydroperoxide, tertiary-butyl peroctoate, acetyl peroxide, etc.

The amount of peroxide present in the reactor relative to the amount of phenothiazine component in the reactor will determine the rate of reaction. Usually it is preferred to add the peroxide to the reactor containing the charge of phenothiazine component at a controlled rate to maintain the reaction speed at the desired rate. The amount of peroxide in the reactor is usually maintained in the range of about 1 to 50 mole percent and preferably in the range of about 5 to 25 mole percent, based on the total number of moles of phenothiazine component present in the reactor.

The dimers can be prepared by heating the phenothiazine component and organic peroxide directly, but, since the phenothiazine component and many organic peroxides are solid, it is usually preferable to carry out the reaction in the presence of a solvent or diluent. Typical diluents include the lower alkanes, petroleum distillate, kerosene, etc. Solvents for the reaction include the aromatic hydrocarbons, such as benzene, toluene, xylene, etc.; ketones, such as methyl ethyl ketone; aldehydes, such as benzaldehydes, etc. Ideally the solvent or diluent is a substance which will not interfere with the intended end use of the product so that there will be no need to recover the dimer from the solvent or diluent prior to the end use. When the reaction is carried out in the presence of a solvent or a diluent, the solvent or diluent is generally present in amounts of about 70 to 97%, based on the total weight of components in the reaction zone.

In a typical procedure for preparing the dimers used in the invention the phenothiazine component and solvent or diluent are charged to a suitable reactor. The desired amount of organic peroxide is then charged to the reactor and the reactor contents are heated to the reaction temperature. If desired, the reaction may be carried out under a nitrogen blanket. As the peroxide is consumed additional peroxide is added to the reactor, either continuously or incrementally, at a rate to control the progress of the reaction. Since the reaction is exothermic it may be necessary to cool the reactor during the course of the reaction. It is usually desirable to agitate the reactor contents during the reaction to dissipate the heat generated during the reaction and to provide a smooth and rapid reaction. The reaction is usually complete in about 2 to 24 hours, depending, of course, on the reaction conditions. Excess peroxide may be added to the reactor to ensure that all of the phenothiazine component is reacted. Upon completion of the reaction, the product may be recovered from the solvent or used as is.

The antifoulants of the invention are particularly well suited for protecting the reboiler sections of a distillation column because of the high boiling point of the antifoulant compounds in the system. The antifoulant system may be used at temperatures up to about 400° C. or higher at atmospheric pressure. In some cases it may be desirable to use lower boiling antifoulants in combination with the antifoulants of the invention. This can advantageously provide protection to the overhead portion of the column. It may also be desirable to add with the antifoulants of the invention other agents, such as corrosion inhibitors, to provide additional protection to process equipment.

The antifoulants of the invention can be introduced into the equipment to be protected by any conventional method. They are generally introduced just upstream of the point of desired application by any suitable means, such as by the use of a proportionating pump. They can be added to the feedstream as a single composition containing all of the desired antifoulant compounds, or the individual components can be added separately or in any other desired combination. The antifoulant may be added as a concentrate, if desired, but it is preferable to add it as a solution which is compatible with the monomer being treated. Suitable solvents include kerosene, naphtha, the lower alkanes such as hexane, aromatic solvents, such as toluene, alcohols, ketones, etc. The concentration of antifoulant system in the solvent is desirably in the range of about 1 to 30 weight percent and preferably about 5 to 20 weight percent based on the total weight of antifoulant and solvent.

The antifoulant is used at a concentration which is effective to provide the desired protection against hydrocarbon fouling. It has been determined that amounts of antifoulant in the range of about 0.5 to 1000 ppm based on the weight of the hydrocarbon feedstream afford ample protection against fouling. For most applications the antifoulant system is used in amounts in the range of about 1 to 500 ppm.

The following example will serve to further illustrate the invention. Unless otherwise stated, parts and percentages are on a weight basis. In the example the thermal fouling determinations were made using a Jet Fuel Thermal Oxidation Tester marketed by Alcor, Inc. The specifications of this apparatus are set forth in ASTM D3241-74T. In general the apparatus consists of a reservoir to hold the hydrocarbon liquid being tested, an electrically heated tubular heater and a precision stainless steel filter. Tubular conduit connects the reservoir with the heater and the heater with the filter. Pressure gauges are provided for measuring the pressure drop across the filter. A thermocouple and a temperature controller are provided for precise control of the temperature of the liquid passing through the heater.

In operation, a hydrocarbon oil is pumped through the heater, which has adequate heat transfer surface to maintain the heater effluent at a predetermined temperature in the range of about 250° to 900° F. As the hydrocarbon passes through the heater a film of polymeric residue builds up on the inside of the heater. Particles of the residue slough off the surface of the heater tube and are caught in the filter. As the filter clogs up the pressure drop across the filter increases. The fouling rate in the heater is approximated by measuring the rate of pressure build-up across the filter. The test is terminated when the pressure drop reaches a predetermined value. The equipment is dismantled and thoroughly cleaned after each run.

In the following example antifoulant effectiveness is measured by comparing the time required for the pressure drop of a hydrocarbon stream containing the antifoulant to reach a certain value with the time required for the pressure crop of a stream of the same hydrocarbon but without the antifoulant to reach the same pressure drop value. The hydrocarbon stream used in the examples was the bottoms product obtained from a toluene recovery unit. This product consists primarily of light hydrocarbons, i.e. up to about 8 carbon atoms and is substantially free of non-aromatic hydrocarbons. This feedstock was selected because aromatic streams usually contain higher unsaturated materials which cause fouling in the recovery tower and associated heat exchangers.

EXAMPLE

A series of antifoulant effectiveness tests were conducted using crude toluene as the antifoulant solvent. The tests were carried out using hydrocarbon flow rate through the heater of about 240 ml per hour with the heater effluent temperature maintained at 600° F. The tests were terminated after 150 minutes. Run 1 was carried out using uninhibited hydrocarbon; Runs 2 and 3 were carried out using the same hydrocarbon as was used in Run 1 but modified by the addition of 50 ppm of phenothiazine and 10,10'-diphenothiazine respectively. The results are tabulated in the following table.

TABLE

| Test Time (Minutes) | Pressure Drop Across Filter, mm Hg. | | |
|---|---|---|---|
| | Run 1 (Blank) | Run 2 Phenothiazine | Run 3 10,10'-Diphenothiazine |
| 0 | 0 | 0 | 0 |
| 20 | — | 0 | — |
| 30 | 0 | — | 0 |
| 45 | 2 | 2 | 2 |
| 60 | 29 | 7 | 2 |
| 90 | 52 | 18 | — |
| 110 | 74 | 26 | 5 |
| 120 | 86 | 38 | — |
| 130 | 104 | 46 | 14 |
| 140 | 128 | — | 16 |
| 150 | 164 | 57 | 22 |

The foregoing example illustrates the benefits derived from the use of the antifoulant composition of the invention. In the control (Run 1) the fouling rate was excessive, as shown by the pressure drop of 164 m.m. Hg. at the end of the run. In Run 2 (comparative), in which phenothiazine was used as the antifoulant, the pressure drop at the end of the run was 57 m.m. Hg. In Run 3, in which an antifoulant of the invention was used, the final pressure drop was only 22 m.m. Hg.

Although the invention is described with particular reference to specific examples, it is understood that the invention includes obvious variants. For example, the antifoulant system can be formulated to contain more than one dimeric derivative of phenothiazine. The scope of the invention is limited only by the breadth of the appended claims.

What is claimed is:

1. In a method of inhibiting fouling of hydrocarbon processing equipment during the processing of hydrocarbons at elevated temperatures comprising introducing into the equipment an amount of an antifoulant agent effective to substantially reduce the rate of fouling, the improvement comprising using as the agent at least one derivative of phenothiazine having the structural formula

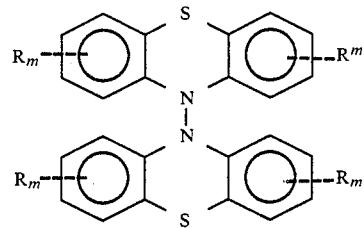

wherein the R's may be the same substitutent or different substituents selected from alkyl groups having 1 to 6 carbon atoms, halogen atoms, halogen-substituted alkyl groups having 1 to 6 carbon atoms and mixtures of these and the m's may be the same integer or different integers in the range of 0 to 4.

2. The process of claim 1 wherein the total concentration of phenothiazine derivative added to said hydrocarbon processing equipment is 0.5 to 1000 ppm, based on the total weight of hydrocarbon being processed in the equipment.

3. The process of claim 2 wherein each m is an integer selected from 0, 1 and 2, each R is an alkyl group having 1 to 6 carbon atoms and the total concentration of phenothiazine derivative added to said hydrocarbon processing equipment is 1 to 500 ppm, based on the total weight of hydrocarbon being processed.

4. The process of claim 3 wherein the antifoulant is 10,10'-phenothiazine.

* * * * *

UNITED STATES PATENT AND TRADEMARK OFFICE
CERTIFICATE OF CORRECTION

PATENT NO. : 4,529,500
DATED : July 16, 1985
INVENTOR(S) : Richard F. Miller and Michael P. Nicholson It is certified that error appears in the above-identified patent and that said Letters Patent is hereby corrected as shown below:

Claim 4, Column 6, Line 52

Word "10,10'-phenothiazine" should read

-- 10,10'-diphenothiazine --

Signed and Sealed this

Twenty-fifth Day of February 1986

[SEAL]

Attest:

DONALD J. QUIGG

Attesting Officer     Commissioner of Patents and Trademarks